US012115189B2

(12) United States Patent
Brown et al.

(10) Patent No.: US 12,115,189 B2
(45) Date of Patent: Oct. 15, 2024

(54) T CELLS FOR EXPRESSION OF CHIMERIC ANTIGEN RECEPTORS AND OTHER RECEPTORS

(71) Applicant: City of Hope, Duarte, CA (US)

(72) Inventors: Christine E. Brown, Duarte, CA (US); Stephen J. Forman, Duarte, CA (US)

(73) Assignee: City of Hope, Duarte, CA (US)

( * ) Notice: Subject to any disclaimer, the term of this patent is extended or adjusted under 35 U.S.C. 154(b) by 802 days.

(21) Appl. No.: 15/746,212

(22) PCT Filed: Jul. 21, 2016

(86) PCT No.: PCT/US2016/043392
§ 371 (c)(1),
(2) Date: Jan. 19, 2018

(87) PCT Pub. No.: WO2017/015490
PCT Pub. Date: Jan. 26, 2017

(65) Prior Publication Data
US 2019/0175648 A1 Jun. 13, 2019

Related U.S. Application Data

(60) Provisional application No. 62/195,254, filed on Jul. 21, 2015.

(51) Int. Cl.
*A61K 35/17* (2015.01)
*A61K 39/00* (2006.01)
*A61P 35/00* (2006.01)
*C07K 14/705* (2006.01)
*C07K 14/725* (2006.01)
*C07K 16/28* (2006.01)
*C12N 5/0783* (2010.01)
*C12N 15/86* (2006.01)

(52) U.S. Cl.
CPC ...... *A61K 35/17* (2013.01); *A61K 39/001112* (2018.08); *A61K 39/001119* (2018.08); *A61P 35/00* (2018.01); *C07K 16/2803* (2013.01); *C07K 16/2866* (2013.01); *C12N 5/0636* (2013.01); *C12N 15/86* (2013.01); *A61K 2039/5156* (2013.01); *A61K 2039/5158* (2013.01); *C07K 14/7051* (2013.01); *C07K 14/70521* (2013.01); *C07K 2317/622* (2013.01); *C07K 2319/03* (2013.01); *C07K 2319/33* (2013.01); *C12N 2501/2302* (2013.01); *C12N 2501/2315* (2013.01); *C12N 2510/00* (2013.01)

(58) Field of Classification Search
None
See application file for complete search history.

(56) References Cited

U.S. PATENT DOCUMENTS

| 2011/0059012 A1 | 3/2011 | Turtle et al. | |
|---|---|---|---|
| 2015/0299656 A1 * | 10/2015 | Gattinoni | A61K 35/17 424/93.71 |

FOREIGN PATENT DOCUMENTS

| CN | 104780939 | 7/2015 | |
|---|---|---|---|
| WO | WO 2002/077029 | 10/2002 | |
| WO | WO-2012129514 A1 * | 9/2012 | A61K 35/17 |
| WO | WO2013014535 A1 | 1/2013 | |
| WO | WO 2014/144622 | 9/2014 | |
| WO | WO2014209855 A1 | 12/2014 | |
| WO | WO 2016/044811 | 3/2016 | |
| WO | WO 2016/044853 | 3/2016 | |

OTHER PUBLICATIONS

Gattinoni et al (Nat Med. 17(10):1290-1297, 2012; PMC Apr. 1, 2012 pp. 1-23).*
Biasco et al. Feb. 4, 2015 vol. 7 Issue 273. In vivo tracking of T cells in humans unveils decade-long survival and activity of genetically modified T memory stem cells (Year: 2015).*
Riddell et al.Journal of Immunological Methods, 128 (1990) 189-201. The use of anti-CD3 and anti-CD28 monoclonal antibodies to clone and expand human antigen-specific T cells (Year: 1990).*
International Application No. PCT/US2016/43392, Notification of Transmittal of the International Search Report and the Written Opinion of the International Searching Authority, mailed Oct. 13, 2016, 10 pages.
Klebanoff et al., "Sorting through subsets: Which T cell populations mediate highly effective adoptive immunotherapy", J. Immunother., Nov. 2012; 35(9): 651-660.
Ciera et al., "IL-7 and IL-15 instruct the generation of human memory stem T cells from naïve precursors," Blood, Jan. 24, 2013, 121(4):573-584.
Wang et al., "CS-1 Re-Directed Central Memory T Cell Therapy for Multiple Myeloma," Blood, American Society of Hematology, Dec. 9, 2014, 124(21):XP009189090.

(Continued)

*Primary Examiner* — Amy E Juedes
*Assistant Examiner* — Brian Hartnett
(74) *Attorney, Agent, or Firm* — Fish & Richardson P.C.

(57) ABSTRACT

Methods for preparing T cell populations useful for a variety of purposes requiring a highly active, long-lived T cell population. The T cell populations are enriched for: naive T cells (TN), memory stem cells (TSCM) and central memory T cells (TCM). These cell populations can be derived from peripheral blood mononuclear cells (PBMC) by both: 1) depleting unwanted cell populations such as CD14 expressing myeloid cells and CD25 expressing cells; and 2) enriching for CD62L expressing memory and naive T cells.

7 Claims, 15 Drawing Sheets

(56) References Cited

OTHER PUBLICATIONS

Xu et al., "Closely related T-memory stem cells correlate with in vivo expansion of CAR.CD19-T cells and are preserved by IL-7 and IL-15," Blood, Apr. 29, 2014, 123(24)3750-3759.
Xu et al., "The roles of stem cell memory T cells in hematological malignancies," Journal of Hematology & Oncology, Oct. 14, 2015, 8(1).
International Preliminary Report on Patentability in International Application No. PCT/US2016/043392, dated Jan. 23, 2018, 9 pages.
Berger et al., "Adoptive transfer of effector CD8+ T cells derived from central memory cells establishes persistent T cell memory in primates," Journal of Cellular Immunology, 2008, 118(1):294-305.
Wang et al., "Engraftment of human central memory-derived effector CD8+ T cells in immunodeficient mice," Blood, 2011, 117:1888-1898.
Wang et al., "Phenotypic and functional attributes of lentivirus-modified CD 19-specific human CD8+ central memory T cells manufactured at clinical scale," J Immunotherapy., 2012, 35:689-701.
Graef et al., "Serial transfer of single-cell-derived immunocompetence reveals stemness of CD8(+) central memory T cells," Immunity, 2014, 41:116-126.
Gattioni et al., "Memory T cells officially join the stem cell club," Immunity, 2014, 41(1):7-9.

\* cited by examiner

1) PBMC

2) $T_{CM}$  Deplete: CD45RA-/CD14-/CD25-
Select: CD62L+

3) $T_{CM/SCM/N}$  Deplete: CD14-/CD25-
Select: CD62L+

T CELLS FOR EXPRESSION OF CHIMERIC ANTIGEN RECEPTORS AND OTHER RECEPTORS

CROSS-REFERENCE TO RELATED APPLICATIONS

This application is a National Stage Application under 35 U.S.C. § 371 and claims the benefit of International Application No. PCT/US2016/043392, filed Jul. 21, 2016, which claims priority to U.S. Provisional Patent Application No. 62/195,254, filed Jul. 21, 2015. The disclosures of each of the foregoing applications are hereby incorporated by reference in their entirety.

BACKGROUND

Adoptive T cell therapy (ACT) utilizing ex vivo expanded autologous and allogeneic T cells is an attractive therapeutic approach for the treatment of viral infection, cancer and autoimmune disease. Methods that enable the rapid generation of large numbers of therapeutic T cells are critical to the potency and safety of ACT. Various T cell enrichment methods, including selection of defined T cell subsets, as well as expansion methods have been used for ACT. It is desirable to employ a T cell population that permits relatively high activity in vivo and relatively high proliferation potential.

SUMMARY

Described herein is a method for preparing T cell populations useful for expressing chimeric antigen receptors ("CARs") for ACT. The T cell populations are also useful for a variety of other purposes requiring a highly active, long-lived T cell population. The T cell populations prepared by the methods described herein are enriched for: naïve T cells ($T_N$), memory stem cells ($T_{SCM}$) and central memory T cells ($T_{CM}$). Thus, such cell populations can be described as $T_{CM/SCM/N}$ cells or $T_{CM/SCM/N}$ cell populations. These cell populations can be derived from peripheral blood mononuclear cells (PBMC) by both: 1) depleting unwanted cell populations such as CD14 expressing myeloid cells and CD25 expressing cells; and 2) enriching for CD62L expressing memory and naïve T cells. Thus, the resulting population of cells includes T naïve ($T_N$) and stem memory cells ($T_{SCM}$) expressing CD45RA and CD62L. It also includes the population of central memory T cells ($T_{CM}$) that express CD45RO and CD62L. $T_{CM/SCM/N}$ cell populations differ from previously described $T_{CM}$ cell populations in that their preparation does not entail depletion of CD45RA+ T cells. $T_{CM/SCM/N}$ cell populations, upon preparation, are relatively free of effector memory cells ($T_{EM}$) and effector cells ($T_E$). Of course, as a $T_{CM/SCM/N}$ cell population undergoes expansion, differentiation will occur, giving rise to, for example, $T_E$ cells.

Patient-specific, autologous and allogeneic $T_{CM/SCM/N}$ cells (or allogenic $T_{CM/SCM/N}$ cells) can be engineered to express a chimeric antigen receptor (CAR) or T cell receptor (TCR) and the engineered cells can be expanded and used in ACT.

Described herein is an isolated population of human cells comprising T cells (i.e., cells that express CD3 or CD3+ cells), wherein the T cells comprise central memory T cells; memory stem T cells, and naïve T cells, wherein greater than 40% (greater than 45%, 50%, 55%, 60%, 65% or 70%) of the T cells are CD45RA+ and greater than 70% (greater than 75%, 80%, 85% or 90%) of the T cells are CD62L+. In various embodiments: less than 15% (less than 12%, 10%, 8%, or 6%) of the T cells are CD14+ and less than 5% (less than 4%, 3% or 2%) of the T cells are CD25+; greater than 10% (greater than 15%, 20%, 25%, 30%, 35%, or 40%) of the T cells harbor a recombinant nucleic acid molecule (e.g., a recombinant nucleic acid molecule such encoding a chimeric antigen receptor or T cell receptor; e.g., a viral vector such as a T cell vector); at least 40% (greater than 45%, 50%, 55%, 60%, 65% or 70%) of the T cells are CD4+ and CD62L+ or CD8+ and CD62L+; at least 10% (greater than 15%, 20%, 25%, 30%, 35%, or 40%) of the T cells are CD8+ and CD62L+; less than 60% (less than 55%, 50%, 45%, 40%, 35%, 30%, 24%, 20% or 15%) of the T cells are CD45RO+; and at least 80% (greater than 85%, 90%, 95%, or 98%) of the cells in the isolated population of cells comprising T cells are T cells.

Also described herein is isolated population of cells comprising human T cells (i.e., cells that express CD3 or CD3+ cells), wherein the T cells comprise central memory T cells and memory stem T cells, wherein greater than 40% (greater than 45%, 50%, 55%, 60%, 65% or 70%) of the T cells are CD45RA+, greater than 40% (greater than 45%, 50%, 55%, 60%, 65%, 70%75%, 80%, 85% or 90%) of the T cells are CD62L+, greater than 70% (greater than 75%, 80%, 85% or 90%) of the T cells are CD95+, and greater than 10% (greater than 15%, 20%, 25%, 30%, 35%, or 40%) of the T cells harbor a recombinant nucleic acid molecule (e.g., a recombinant nucleic acid molecule (e.g., a viral vector) encoding, e.g., a chimeric antigen receptor or T cell receptor). In various embodiments: less than 15% (less than 12%, 10%, 8%, 6%) of the T cells are CD14+ and less than 5% (less than 4%, 3% or 2%) of the T cells are CD25+; at least 40% (greater than 45%, 50%, 55%, 60%, 65% or 70%) of the T cells are CD4+ and CD62L+ or CD8+ and CD62L+; at least 10% (greater than 15%, 20%, 25%, 30%, 35%, or 40%) of the T cells are CD8+ and CD62L+; less than 60% (less than 55%, 50%, 45%, 40%, 35%, 30%, 24%, 20% or 15%) of the T cells are CD45RO+; and at least 80% (greater than 85%, 90%, 95%, or 98%) of the cells in the isolated population of cells comprising T cells are T cells.

Described herein is a method for preparing a population of human cells comprising T cells (i.e., cells that express CD3 or CD3+ cells) harboring a recombinant nucleic acid molecule, comprising: (a) providing a sample of human cells comprising T cells, wherein the T cells comprise: central memory T cells; memory stem T cells, and naïve T cells, wherein greater than 40% (greater than 45%, 50%, 55%, 60%, 65% or 70%) of the T cells are CD45RA+ and greater than 70% (greater than 75%, 80%, 85% or 90%) of the T cells are CD62L+; (b) activating the population of human cells comprising T cells; and (c) transducing or transfecting cells in the population of human cells comprising T cells with a recombinant nucleic acid molecule to provide a population of human cells comprising T cells harboring a recombinant nucleic acid molecule, wherein the method does not comprise a step of depleting cells expressing CD45RA. In various embodiments: the recombinant nucleic acid molecule is a viral vector (e.g., a lentiviral vector, a viral vector encoding a CAR, a viral vector encoding a T cell receptor); the method further comprises culturing the population of human cells comprising T cells harboring a recombinant nucleic acid molecule; the culturing step comprises the addition of exogenous IL-2 and exogenous IL-15; and the activating step comprises exposing the cells to an anti-CD3 antibody and an anti-CD28 antibody; and at least 80% (greater than 85%, 90%, 95%, or 98%) of the cells in the isolated population of cells comprising T cells are T cells.

Described herein is method for preparing a population of human cells comprising T cells (i.e., cells that express CD3 or CD3+ cells), wherein the T cells comprise central memory T cells; memory stem T cells, and naïve T cells, wherein greater than 40% (greater than 45%, 50%, 55%, 60%, 65% or 70%) of the cells are CD45RA+ and greater than 70% (greater than 75%, 80%, 85% or 90%) are CD62L+, comprising: (a) providing an isolated population of human cells comprising T cells; (b) treating the isolated population of human cells comprising T cells to deplete cells expressing CD25 and cells expressing CD14 to prepare a depleted cell population; and (c) treating the depleted cell population to enrich for cells expressing CD62L, thereby preparing a population of human cells comprising T cells, wherein the T cells comprise central memory T cells; memory stem T cells, and naïve T cells, wherein greater than 40% of the cells are CD45RA+ (greater than 45%, 50%, 55%, 60%, 65% or 70%) and greater than 70% are CD62L+, wherein the method does not comprise a step of depleting cells expressing CD45RA. In various embodiments: the method further comprises activating the population of human cells comprising T cells and transducing or transfecting the activated cells with a recombinant nucleic acid molecule to provide a population of T cells comprising T cells harboring a recombinant nucleic acid molecule; isolated population of human cells comprising T cells comprises PBMC; and at least 80% (greater than 85%, 90%, 95%, or 98%) of the cells in the isolated population of cells comprising T cells are T cells.

Also described herein is a population of human cells comprising T cells (i.e., cells that express CD3 or CD3+ cells), wherein the T cells comprise central memory T cells; memory stem T cells, and naïve T cells, wherein greater than 40% (greater than 45%, 50%, 55%, 60%, 65% or 70%) of the cells are CD45RA+ and greater than 70% (greater than 75%, 80%, 85% or 90%) are CD62L+, wherein the population is prepared by a method comprising: providing an isolated population of human cells comprising T cells (e.g. PBMC from a donor); treating the isolated population of human cells comprising T cells to deplete cells expressing CD25 and deplete cells expressing CD14 to prepare a depleted cell population; and treating the depleted cell population to enrich for cells expressing CD62L, thereby preparing a population of human cells comprising T cells, wherein the T cells comprise central memory T cells; memory stem T cells, and naïve T cells, wherein greater than 40% (greater than 45%, 50%, 55%, 60%, 65% or 70%) of the cells are CD45RA+ and greater than 70% (greater than 75%, 80%, 85% or 90%) are CD62L+, wherein the method does not comprise a step of depleting cells expressing CD45RA. In various embodiments: less than 15% (less than 12%, 10%, 8%, 6%) of the T cells in the population of human cells are CD14+ and less than 5% (less than 4%, 3% or 2%) of the T cells are CD25+; at least 40% (greater than 45%, 50%, 55%, 60%, 65% or 70%) of the T cells are CD4+ and CD62L+ or CD8+ and CD62L+; at least 10% (greater than 15%, 20%, 25%, 30%, 35%, or 40%) of the T cells are CD8+ and CD62L+; less than 60% (less than 55%, 50%, 45%, 40%, 35%, 30%, 24%, 20% or 15%) of the T cells are CD45RO+

Also described herein is a method of treating cancer, autoimmunity or infection comprising administering to a patient in need thereof a pharmaceutical composition comprising a human cell population described herein. In some cases the cells are autologous to the patient being treated and in some cases they are alloegenic to the patient being treated.

A cell population can be depleted for cells expressing a particular marker (e.g., receptor) by removing (using for example a selective antibody and cells sorting methods) some, most or nearly all of the cells expressing the marker from the population of cells so that the relative proportion of the cells in the population expressing the marker is reduced. A cell population can be enriched for cells expressing a particular marker (e.g., receptor) by collecting (using for example a selective antibody and cells sorting methods) some, most or nearly all of the cells expressing the marker from the population of cells and discarding cells not expressing the marker so that the relative proportion of the cells in the population expressing the marker is reduced.

DETAILED DESCRIPTION

The T cell compartment includes T cell subsets that are at different stages of differentiation. These subsets arise from differentiation of Nave T cells ($T_N$), which are CD45RA+, CD62L+, CD28+, and CD95-. Among the stem cell-like subsets are Memory Stem Cells ($T_{SCM}$), which are CD45RA+, CD62L+, CD28+, and CD95+. These cells differentiate into Central Memory Cells ($T_{CM}$), which are CD45RO+, CD62L+, CD28+, and CD95+. $T_{CM}$ differentiate in Effector Memory Cells ($T_{EM}$), which are CD45RO+, CD62L-, CD28+/-, and CD95+. The $T_{EM}$ differentiate to Effector T cells ($T_E$) which are CD45RO+, CD62L+, CD28+, and CD95+.

Figure 1:
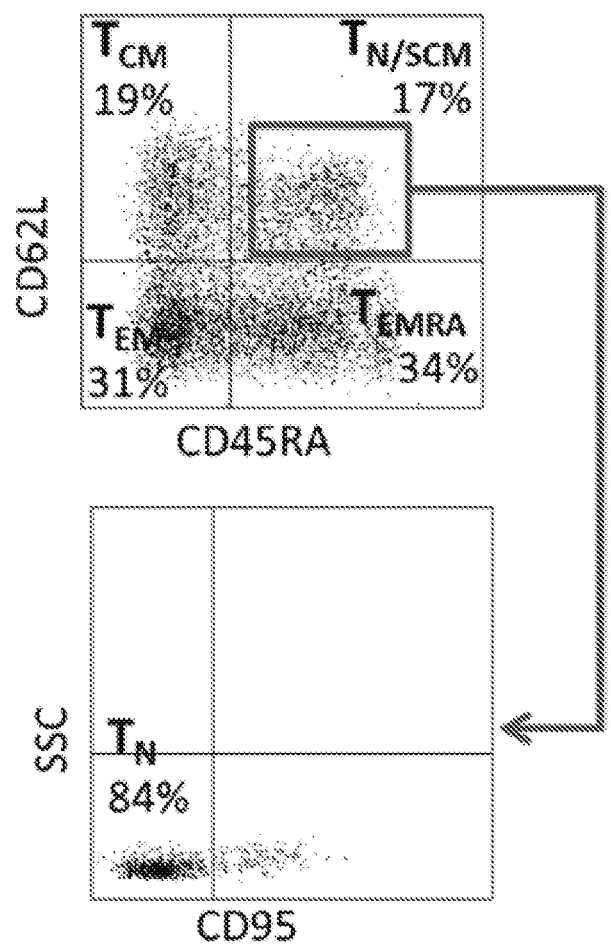
FIG. 1 depicts certain marker expression patterns for various T cell subsets, particularly expression patterns that distinguish $T_{SCM}$ form $T_N$.

Memory Stem T Cells ($T_{SCM}$) are present at a low level in the T cell compartment, but appear to have significant self-renewal and proliferative potential. While they resemble naïve T cells ($T_N$) in that they express CD45RA+ and CD62L+, they can be distinguished from $T_N$ by their expression of CD95 (FIG. 1). $T_{SCM}$ can be generated from $T_N$ by stimulation with CD3/CD28 beads in the presence of IL-7 and IL-15. They also can be expanded in the presence of Wnt/β-catenin pathway activation.

Figure 2:
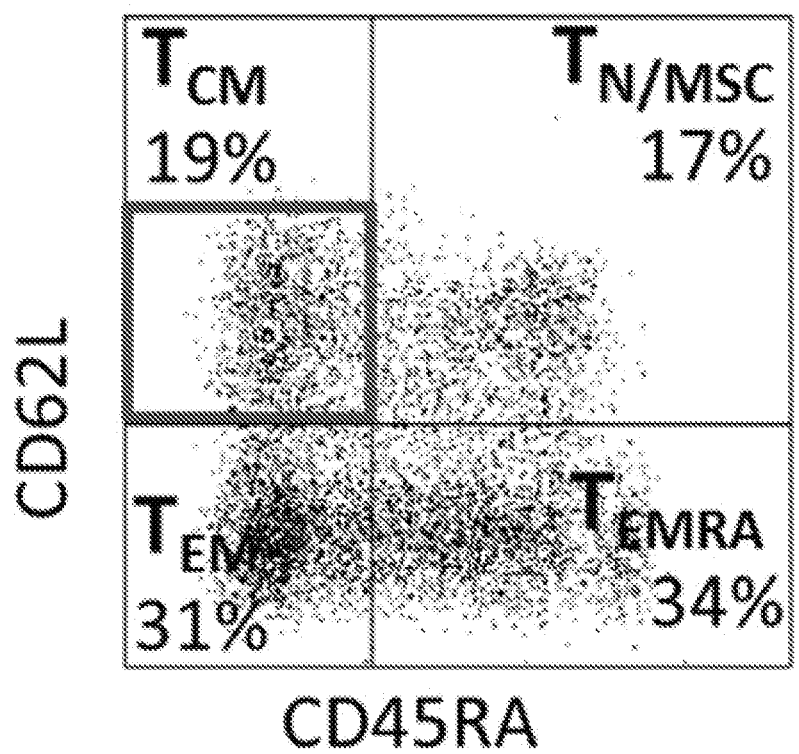
FIG. 2 depicts certain marker expression data for various T cell subsets.

Central Memory T Cells ($T_{CM}$), which are more abundant in PBMC than are $T_{SCM}$, are a well-defined memory T cell subset with high self-renewal and proliferative potential. There is evidence that $T_{CM}$ persist following adoptive transfer better than Effector T cells ($T_E$) (Berger et al., 2008 *Journal of Cellular Immunology* 118:4817; Wang et al., 2011 *Blood* 117:1888). $T_{CM}$ can be enriched from PBMC for T cell therapy manufacturing based on their CD45RA-CD45RO+ CD62L+ phenotype (FIG. 2) Wang X et al. *J Immunotherapy* 2012; 35:689. There is some evidence that $T_{CM}$ behave as adult stem cells. Studies in mice demonstrated that: single cell transfer of $T_{CM}$ over three generations demonstrated that $T_{CM}$ can provide full immune reconstitution; that $T_{CM}$ expand to produce more $T_{CM}$; and that $T_{CM}$ differentiate to $T_{EM}/T_E$ (Graef et al. 2014 *Immunity* 41:116; Gattioni et al. 2014 *Immunity* 41:7).

Figure 3:
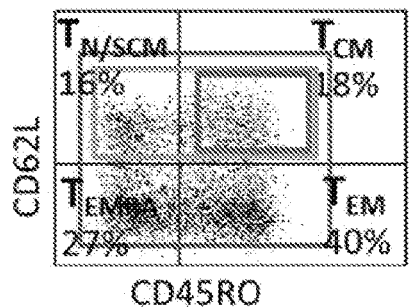
FIG. 3 depicts the relationships between certain T cell subsets based on expression of CD62L and CD45RO.

The $T_{CM/SCM/N}$ cell population described below includes $T_{CM}$, which have proven efficacy in CAR-T therapy, and $T_N$ as well as $T_{SCM}$, both of which are more stem cell-like than $T_{CM}$. FIG. 3 presents expression data depicting a relationship between the various cell populations and PBMC.

The cell populations described herein can be genetically engineered to express, for example, a CAR or a T cell receptor. A CAR is a recombinant biomolecule that contains an extracellular recognition domain, a transmembrane region, and one or more intracellular signaling domain. The term "antigen," therefore, is not limited to molecules that bind antibodies, but to any molecule that can bind specifically to any receptor. "Antigen" thus refers to the recognition domain of the CAR. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and optionally comprises one or more co-stimulatory signaling domains. CARs can both to bind antigen and transduce T cell activation, independent of MHC restriction. Thus, CARs are "universal" immunoreceptors which can treat a population of patients with antigen-positive tumors irrespective of their HLA genotype. Adoptive immunotherapy using T lymphocytes that express a tumor-specific CAR can be a powerful therapeutic strategy for the treatment of cancer.

The CAR can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, overlapping PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various CAR suitable for expression by $T_{CM/SCM/N}$ cells include, for example, those described in: WO 2016/044811; WO 2104/144622; WO 2002/077029; and WO/US2014/0288961.

Example 1: Preparation of $T_{CM/SCM/N}$ Cells

A variety of methods can be used to produce a population of human $T_{CM/SCM/N}$ cells. For example, a population of $T_{CM/SCM/N}$ cells can be prepared from a mixed population T lymphocytes. The population of T lymphocytes can be allogenic to or autologous to the subject ultimately treated using the cells and can be obtained from a subject by leukopheresis or blood draw.

The following method is an example of one that can be used to obtain a population of $T_{CM/SCM/N}$ cells from T lymphocytes obtained by leukapheresis or other means. Peripheral blood is collected by leukapheresis or peripheral blood draw. Day 1 of a typical manufacturing cycle is the day the ficoll procedure takes place. The subject's leukapheresis product is diluted with EDTA/PBS and the product is centrifuged at 1200 RPM for 10 minutes at room temperature with maximum brake. After centrifugation, the platelet-rich supernatant is removed and the cell pellet is gently vortexed. EDTA/PBS is used to re-suspend the vortexed cell pellets in each conical tube. Each tube is then underlayed with ficoll and centrifuged at 2000 RPM for 20 minutes with no brake at room temperature. Following centrifugation, the PBMC layer from each tube is transferred into another conical tube. The cells are centrifuged at 1800 RPM for 15 minutes with maximum brake at 4° C.

After centrifugation, the cell-free supernatant is discarded and the cell pellet is gently vortexed. The cells are washed twice using EDTA/PBS each time, and a third time using PBS. Cells are centrifuged each time at 1200 RPM for 10 minutes with maximum brake at 4° C. After the final PBS wash, the vortexed cell pellet is resuspended in complete X-VIVO 15 media (X-VIVO™ media with 10% FBS) and transferred to a transfer bag. The bag with washed PBMC is kept overnight on a rotator at room temperature on the bench top for immunomagnetic selection the next day.

Next, selection procedures are used to both to deplete the cell population of cells expressing certain markers and to enrich the cell population for cells expressing certain other markers. These selection steps preferably occur on day two of the manufacturing cycle. The cell population is substantially depleted for cells expressing CD25 and CD14. Importantly, the cell population is not substantially depleted for cells expressing CD45RA. Briefly, cells resuspended in labeling buffer (LB; EDTA/PBS with 0.5% HSA), and incubated with anti-CD14 and anti-CD25 Miltenyi antibodies for CliniMACS® depletion, and the composition is gently mixed and then incubated for 30 minutes on a rotator at room temperature on the bench top.

The depletion step is performed on a CliniMACS® device using a depletion tubing set. The recovered cells following the depletion step are transferred into tubes and centrifuged at 1400 RPM for 15 minutes with maximum brake at 4° C.

The cell-free supernatant is removed and the cell pellet is gently vortexed and resuspended. To enrich for cells expressing CD62L, the cell suspension is treated with anti-CD62L-biotin (made at the City of Hope Center for Biomedicine and Genetics), gently mixed and incubated for 30 minutes on a rotator at room temperature on the bench top.

Following the incubation period, LB is added to the tube and cells are centrifuged at 1400 RPM for 15 minutes at maximum brake at 4° C. The cell-free supernatant is removed and the cell pellet is gently vortexed. LB is added to resuspend the cell pellet in the tube and the resuspended cells are transferred to a new transfer bag. Anti-biotin (Miltenyi Biotec) reagent is added and the mixture is gently mixed and incubated for 30 minutes on a rotator at room temperature on the bench top.

The CD62L enrichment step is performed on a CliniMACS® device using a tubing set. The product of this enrichment can be frozen for storage and later thawed and activated To provide an intermediate holding step in the manufacturing, the option exists to freeze cells following the selection process. The cells are pelleted by centrifugation at 1400 RPM for 15 minutes with max break at 4° C. The cells are resuspended in Cryostor® and aliquoted into cryovials. The vials will transferred to a controlled cooling device that can cool at about 1° C./minute (e.g., a Nalgene® Mr. Frosty; Sigma-Aldrich) the cooling device is immediately transferred to a −80° C. freezer. After three days in the −80° C. freezer, the cells are transferred into a GMP LN2 freezer for storage.

We have found that cryopreserved cells exhibit good recovery and viability, maintain the appropriate cell surface phenotype when thawed up to 8.5 months after cryopreservation, and can be successfully transduced and expanded in vitro upon thawing.

Alternatively, freshly enriched Tcm/scm/n cells can be activated, transduced or expanded as described in Example 3, below.

Example 2: Comparison of $T_{CM}$ and $T_{CM/SCM/N}$ Yield and Recovery

A study was conducted to evaluate the yield of human peripheral blood mononuclear cells (PBMC) that had undergone CliniMACS/AutoMACS™ enrichment of the following T cell populations: 1) CD62L+ central memory ($T_{CM}$) cells, and 2) CD62L+ $T_{CM/SCM/N}$ cells, which includes both the central memory ($T_{CM}$) and stem cell memory ($T_{SCM}$) populations along with naïve T cells ($T_N$). Evaluations were performed using Guava analysis of viable cell numbers and flow cytometric analysis of phenotype.

Experimental Design:

$T_{CM}$ and $T_{CM/SCM/N}$ cell lines were enriched from PBMC collected from healthy human donors. Briefly, $T_{CM/SCM/N}$ cells were produced by CliniMACS/AutoMACS™ depletion of the CD14+ monocytes and the CD25+ regulatory T cells, followed by AutoMACS™ selection of the CD62L+ memory population. In contrast, $T_{CM}$ cells were produced by CliniMACS/AutoMACS™ depletion of the CD14+ monocytes, the CD25+ regulatory T cells, and the CD45RA+ naïve and stem cell memory T cells, followed by AutoMACS™ selection of the CD62L+ population. Evaluation of the selection process included viable cell number enumeration, as well as flow cytometric analysis, described in greater detail below. The cells were then cryopreserved for future studies.

Overview of Enrichment Process:

The blood products were ficolled, and the resulting PBMC underwent a series of washes in PBS/EDTA. PBMC were then resuspended in complete X-Vivo 15 media and, in some cases were transferred to a 300 cc transfer bag that was then placed on a 3-D rotator overnight. The PBMC then underwent sequential rounds of CliniMACS/AutoMACS™ depletion and selection to enrich for either the CD14$^-$/CD25$^-$/CD45RA$^-$/CD62L$^+$ $T_{CM}$ or CD14$^-$/CD25$^-$/CD62L$^+$ $T_{CM/SCM/N}$ populations. The first step involved magnetic depletion (via CliniMACS™ or AutoMACS™) to remove the CD14+ monocytes, the CD25+ regulatory T cells, and, for the $T_{CM}$, the CD45RA+ naïve T cells. The remaining cells then underwent a positive selection (via AutoMACS™) for the CD62L+ population using the Anti-CD62L-Biotin (Dreg 56) reagent. Final cell counts after both rounds of enrichment were recorded. Samples of the final selected cell population were then analyzed by flow cytometry.

Overview of Flow Cytometric Assay and Analysis:

Flow cytometric analysis of cell populations was conducted as follows. Samples were washed in FACS Stain Solution (FSS) using a tabletop centrifuge, resuspended in FSS and 100 µL per sample was aliquoted into pre-labeled 12×75 mm FACS tubes (1 tube per condition). The required volume of antibody was added to their respective FACS tubes and tubes were then incubated for 30 minutes in the dark at 4° C. At the end of incubation each tube was washed twice in FSS and resuspended in either 250 µl FSS, or FSS containing DAPI as a viability dye. Samples were then run and analyzed on a FACS Calibur (Becton Dickenson) or MACSQuant (Miltenyi) instrument. Percentages of viable immunoreactive cells were calculated via FCS Express software (De Novo Software, Los Angeles, CA).

Post-Enrichment Yield:

Recovery of CD3+ T cells from each of the cell products are depicted in Table 1, below. Overall, enrichment of the CD14$^-$/CD25$^-$/CD45RA$^-$/CD62L$^+$ CD3$^+$ $T_{CM}$ resulted in a 2-6% recovery, while enrichment of the CD14$^-$/CD25$^-$/CD62L$^+$ CD3$^+$ $T_{CM/SCM/N}$ resulted in a 4-30% recovery. Indeed, when comparing each matched pair, there was a 1.6- to 15-fold higher recovery of $T_{CM/SCM/N}$ cells vs. $T_{CM}$ cells.

TABLE 1

| Product # | Product Type | Total viable cells (×10$^6$) Input Cell # | Recovered CD3+ Cell # | % Recovery of CD3+ Cells | % CD8+ of Enriched Cells |
|---|---|---|---|---|---|
| HD006.6 | $T_{CM}$ | 3000 | 166 | 6 | 17 |
|  | $T_{CM/SCM/N}$ | 3000 | 302 | 10 | 23 |
| HD007.8 | $T_{CM}$ | 3000 | 48 | 2 | 10 |
|  | $T_{CM/SCM/N}$ | 3000 | 128 | 4 | 28 |
| HD033.4 | $T_{CM}$ | 5000 | 277 | 6 | 27 |
|  | $T_{CM/SCM/N}$ | 5000 | 898 | 18 | 64 |
| HD094.1 | $T_{CM}$ | 4140 | 87 | 2 | 13 |
|  | $T_{CM/SCM/N}$ | 4140 | 1256 | 30 | 27 |
| HD187.2 | $T_{CM}$ | 5000 | 111 | 2 | 26 |
|  | $T_{CM/SCM/N}$ | 5000 | 793 | 16 | 36 |
| HD270 | $T_{CM}$ | 800 | 22 | 3 | 11 |
|  | $T_{CM/SCM/N}$ | 300 | 47 | 16 | 8 |
| HD294 | $T_{CM}$ | 3000 | 96 | 3 | 23 |
|  | $T_{CM/SCM/N}$ | 3000 | 185 | 6 | 40 |

Figure 4:
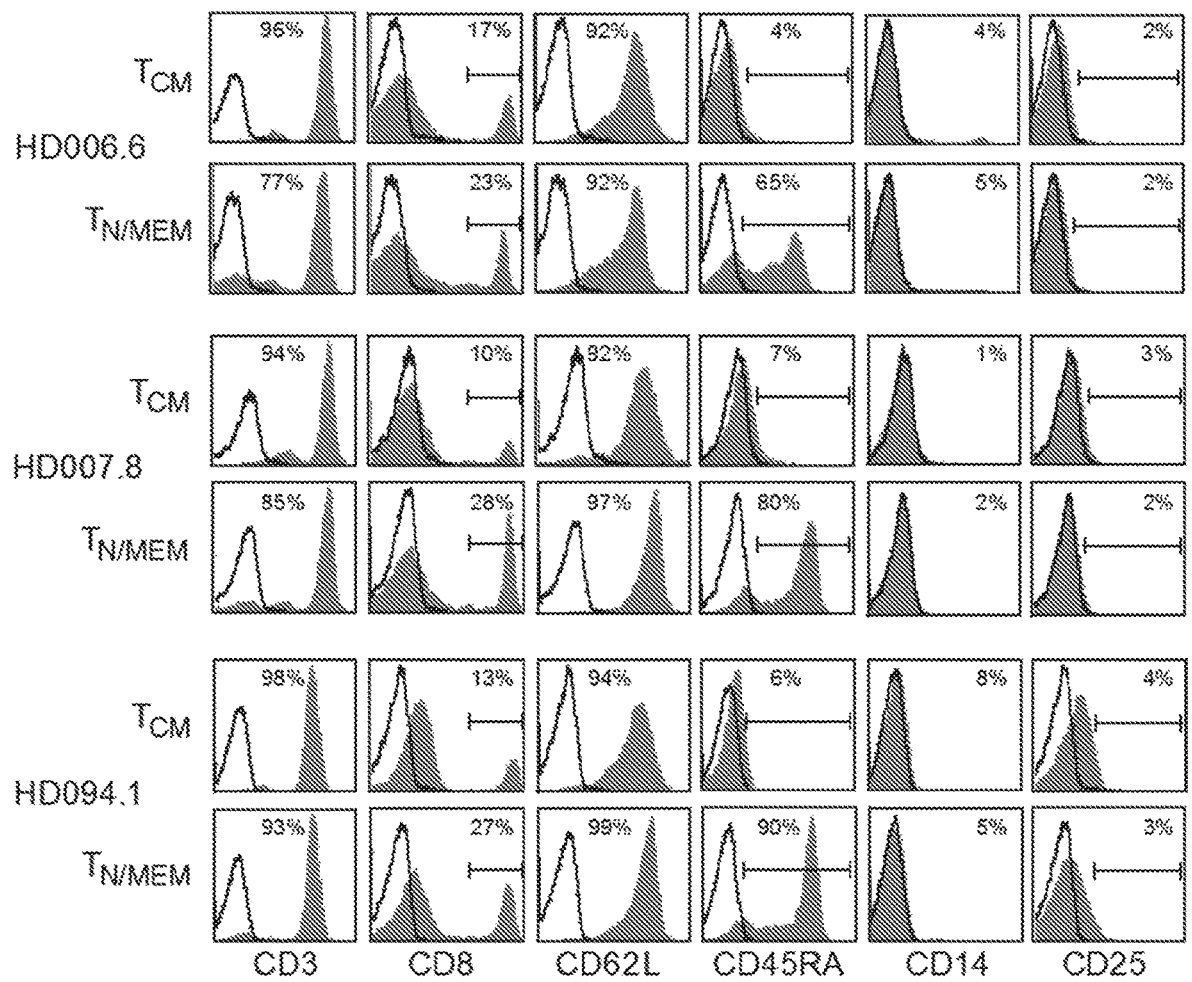
FIG. 4 depicts the results of surface phenotype analysis of cells after CliniMACS™ Enrichment for $T_{CM}$ or $T_{CM/SCM/N}$ cells. Cells from the indicated products were stained with fluorochrome-conjugated antibodies specific for the T cell markers CD3 and CD8, the central memory T cell marker CD62L, and the naïve T cell marker CD45RA, as well as the monocyte marker CD14 and regulatory T cell marker CD25. Percentages of immunoreactive cells (shaded histograms) above isotype control staining (black line) are indicated in each histogram.

Post-Enrichment Flow Cytometric Analysis:

After both rounds of CliniMACS™ enrichment, the phenotype of the enriched cells was determined by FACS analysis. Results of cell products derived from three representative donors are shown in FIG. 4. The $T_{CM}$ and $T_{CM/SCM/N}$ populations from each donor exhibited enriched levels of CD3+ and CD62L+ cells, with the $T_{CM}$ being depleted of CD45RA while the $T_{CM/SCM/N}$ expressed CD45RA as expected. Depletion of the CD14+ and CD25+ populations was also observed as expected with both selection strategies. Interestingly, percentages of CD8+ cells were often higher in the $T_{CM/SCM/N}$ population when compared to its donor-matched $T_{CM}$ population (FIG. 4 and Table 1).

Results:

The results of this study demonstrate that clinically translatable GMP manufacturing methods can be used to efficiently isolate both CD62L+ $T_{CM}$ as well as $T_{CM/SCM/N}$ cell population. Starting from PBMC 2-6% of the starting population is recovered as CD3+ $T_{CM}$. Eliminating the CD45RA-depletion step allows recovery of 4-30% of the starting population as CD3+ $T_{CM/SCM/N}$ cells. The ability to recover 1.6- to 15-fold more $T_{CM/SCM/N}$ cells as compared to $T_{CM}$ cells would increase the number of T cells that can be used as a starting population for genetic engineering. Further, we observed that elimination of the CD45RA depletion step also appeared to increase the percentage of CD8 T cells in the enriched product.

Example 3: Lentiviral Transduction of $T_{CM/SCM/N}$ Cells

A $T_{CM/SCM/N}$ cell population can be genetically engineered to express protein or proteins of interest. For example, the cells can be transduced with a lentivirus capable of expressing a protein or proteins of interests. The following is an example of one method that can be used to transduce the T cells with a lentivirus vector with protamine sulfate/cytokine solution.

If the cells are frozen subsequent to the selection process, the cells will need to be thawed upon continuation of the manufacturing process. The cryopreserved vials are thawed in a 37° C. water bath until mostly liquid remains. The contents of the vials are placed in a conical tube containing cold X-Vivo 15 media. The cells are centrifuged at 1200 RPM for 10 minutes with max brake at 4° C. After centrifugation, the cell-free supernatant is decanted, the pellets are vortexed, and all the pellets combined into one tube in X-Vivo 15 media to be transduced with lentivirus. The cell numbers are determined and the manufacturing process continues with Dynal bead activation.

The cells are centrifuged at 1400 RPM for 10 minutes at 25° C. After centrifugation, the cell-free supernatant is removed and the cell pellet is gently vortexed and resuspended in complete X Vivo 15 media to be transduced with lentivirus. If thawed cells are being used, the centrifugation step is not necessary.

Tcm/scm/n cells are stimulated with Dynabeads® Human T expander CD3/CD28 (Invitrogen) at a 1:3 ratio (T cell:bead), then cultured in the presence of 50 U/mL rhIL-2 (Chiron) and 0.5 ng/ml rhIL-15 (CellGenix).

After a one to three day incubation, T cells are transduced with the lentiviral vector at a MOI typically ranging from 0.1 to 1.5 in X Vivo15 containing 10% FCS with 5 µg/mL protamine sulfate (APP Pharmaceutical), 50 U/mL rhIL-2 and 0.5 ng/mL rhIL-15. The day following the lentivirus transduction, one volume of media is added of freshly prepared media/cytokine mastermix containing complete X-VIVO 15 media and cytokines (10 µL rhuIL-2 and 0.5 µL rhuIL-15).

Cultures are then maintained at 37° C., 5% $CO_2$ in X-Vivo15 10% FCS as required to keep cell density between $3\times10^5$ and $2\times10^6$ viable cells/mL, with cytokine supplementation (final concentration of 50 U/mL rhIL-2 and 0.5 ng/mL rhIL-15) every Monday, Wednesday and Friday of culture.

CD3/CD28 Dynabead removal takes between days 7 to 9 after bead stimulation. The Dynal beads are removed using the DynaMag-50 or MPC magnet. After bead removal, a sample of the cell suspension is taken for counts. Based on the counts, the concentration is adjusted to approximately $0.5 \times 10^6$/mL.

Cultures are propagated until sufficient numbers of cells are achieved, which is typically between 8 and 18 days. During this time, a full replacement of cytokines are added to the T cell cultures. Starting on day 12 and every Monday, Wednesday and Friday thereafter, counts are taken to maintain a concentration of approximately $0.5 \times 10^6$ cells/mL Final harvest and cryopreservation proceeds as follows. The cell product is cryopreserved once the expanded cells reach the necessary number of viable cells required for clinical administration or research purposes. The cells are counted and in-culture samples are harvested for mycoplasma testing. The remaining cells are centrifuged at 1800 RPM for 20 minutes, maximum brake at 4° C. The cell-free supernatant is removed and all cell pellets are gently vortexed, resuspended and combined into Isolyte buffer (Braun). The tube is centrifuged at 1800 RPM for 20 minutes, max brake at 4° C. The cells are resuspended in Isolyte for a second wash.

After the second Isolyte wash, the cell-free supernatant is removed and the cell pellet is gently vortexed and resuspended in an appropriate volume of the cryopreservation media, CryoStor® 5 (BioLife Solutions), in order to have cells at an appropriate concentration. Cells are cyropresserved by placing in a controlled cooling device that can cool at about 1° C./minute (e.g., a Nalgene® Mr. Frosty; Sigma-Aldrich) or a control rate freezer system (Custom Biogenics). At completion of the freeze procedure, the cassette(s)/bag(s) and cryovials are immediately transferred into a LN2 freezer for storage.

Example 4: Comparison of $T_{CM}$ and $T_{CM/SCM/N}$ Cells that have been Bead-Stimulated, Lentivirally Transduced and Expanded A study was conducted to evaluate the ex vivo expansion and cell surface phenotype of human peripheral blood mononuclear cells (PBMC) that had undergone CliniMACS/AutoMACS™ enrichment for either the CD62L+ $T_{CM}$ population, or the CD62L+ $T_{CM/SCM/N}$ population (which includes nave, central memory, and stem cell memory T cells), followed by bead stimulation and lentiviral transduction with either the CD19R(EQ)28Z-T2A-EGFRt_epHIV7, a lentivirus expressing a CAR targeted to CD19R or IL13 (EQ)BBZ-T2A-CD19t_epHIV7, lentiviral vector targeted to IL-13Ralpla (see WO 2016/044811 and WO/2002/077029 for details of the vectors and expressed CARs), using methods proposed for clinical use. Expansion was evaluated by monitoring of viable cell numbers and cell surface phenotype was evaluated by flow cytometric analysis.

Experimental Design:

Chimeric antigen receptor (CAR) T cell products originating from the PBMC of three separate human donors were generated using methodologies expected to be suitable for clinical use. Briefly, $T_{CM}$ and $T_{CM/SCM/N}$ cells that had been enriched from PBMC (essentially as described above in Example 2) were activated by CD3/CD28-bead stimulation and transduced with either CD19R(EQ)28Z-EGFRt_epHIV7 or IL13(EQ)BBZ-T2A-CD19t_epHIV7 lentivirus. The CD3/CD28 beads were removed after 7-9 days, and T cell cultures were then expanded in accordance and maintained for up to 29 days with addition of complete X-VIVO 15 media as required by cell expansion (keeping cell density between $0.3 \times 10^6$ and $2 \times 10^6$ viable cells/mL). Cytokines were supplemented every Monday, Wednesday and Friday of culture. Viable cell numbers were monitored during this expansion process. Final cell products were then evaluated for the surface markers traditionally used for cell product release, e.g., CD3 and either truncated EGFR (EGFRt) or truncated CD19 (CD19t) as a transduction marker, as well as the T cell markers CD4, CD8, CD27, CD28, CD45RA and CD62L.

Overview of Stimulation, Transduction and Expansion:

Enriched $T_{CM}$ or $T_{CM/SCM/N}$ cells were CD3/CD28-bead activated and lentivirally transduced with GMP-grade CD19R(EQ)28Z-T2A-EGFRt_epHIV7 or either GMP-grade or research-grade IL13(EQ)BBZ-T2A-CD19t_epHIV7 at a multiplicity of infection (MOI) between 0.3 and 3.0. The cells were put into culture in complete X-Vivo 15 media with rhIL-2 at 50 U/mL and rhIL-15 at 0.5 ng/mL. Cultures were then maintained with addition of complete X-Vivo15 media as required to keep the cell density between $0.3 \times 10^6$ and $2 \times 10^6$ viable cells/mL, and with cytokine supplementation (rhIL-2 and rhIL-15) every Monday, Wednesday and Friday of culture. After seven to nine days of bead stimulation, the CD3/CD28 Dynabeads were removed from cultures using the DynaMag-50 magnet. Viable cell numbers were monitored during this expansion process, and viable cell counts during culture and on the final day of cryopreservation were recorded. The various products are listed in Table 2.

TABLE 2

Manufacturing Overview

| Product Source | Lentiviral Vector Used (MOI) | Product Name |
| --- | --- | --- |
| HD033.4 $T_{CM}$ | CD19R(EQ)28Z-EGFRt_epHIV7 (1.0) | HD033.4 CD19R $T_{CM}$ |
| HD033.4 $T_{CM/SCM/N}$ | CD19R(EQ)28Z-EGFRt_epHIV7 (1.0) | HD033.4 CD19R $T_{CM/SCM/N}$ |
| HD187.2 $T_{CM}$ | CD19R(EQ)28Z-EGFRt_epHIV7 (0.5) | HD187.2 CD19R $T_{CM}$ |
|  | IL13(EQ)BBZ-T2A-CD19t_epHIV7 (0.3) | HD187.2 IL13R $T_{CM}$ |
| HD187.2 $T_{CM/SCM/N}$ | CD19R(EQ)28Z-EGFRt_epHIV7 (0.5) | HD187.2 CD19R $T_{CM/SCM/N}$ |
|  | IL13(EQ)BBZ-T2A-CD19t_epHIV7 (0.3) | HD187.2 IL13R $T_{CM/SCM/N}$ |
| HD270 $T_{CM}$ | CD19R(EQ)28Z-EGFRt_epHIV7* (3.0) | HD270 CD19R $T_{CM}$ |
|  | IL13(EQ)BBZ-T2A-CD19t_epHIV7 (0.3) | HD270 IL13R $T_{CM}$ |
| HD270 $T_{CM/SCM/N}$ | CD19R(EQ)28Z-EGFRt_epHIV7* (3.0) | HD270 CD19R $T_{CM/SCM/N}$ |
|  | IL13(EQ)BBZ-T2A-CD19t_epHIV7 (0.3) | HD270 IL13R $T_{CM/SCM/N}$ |

Flow Cytometry:

Samples were washed in FACS Stain Solution (FSS) using a tabletop centrifuge, resuspended in FSS and 100 μL per sample was aliquoted into pre-labeled 12×75 mm FACS tubes (1 tube per condition). The required volume of antibody was added to their respective FACS tubes and tubes were then incubated for 30 minutes in the dark at 4° C. In some cases, samples were washed and then stained with fluorochrome-conjugated straptavidin as a secondary reagent. At the end of incubation each tube was washed twice in FSS and resuspended in either 250 μl FSS, or in 140 μL FSS and 70 μL working dilution of DAPI (made by mixing 6.9 μL of the stock with 25 mL of FSS). Samples were then run and analyzed on a FACS Calibur (Becton Dickenson) or MACSQuant (Miltenyi) instrument. Percentages of immunoreactive cells were calculated via FCS Express software (De Novo Software, Los Angeles, CA).

Figure 5:
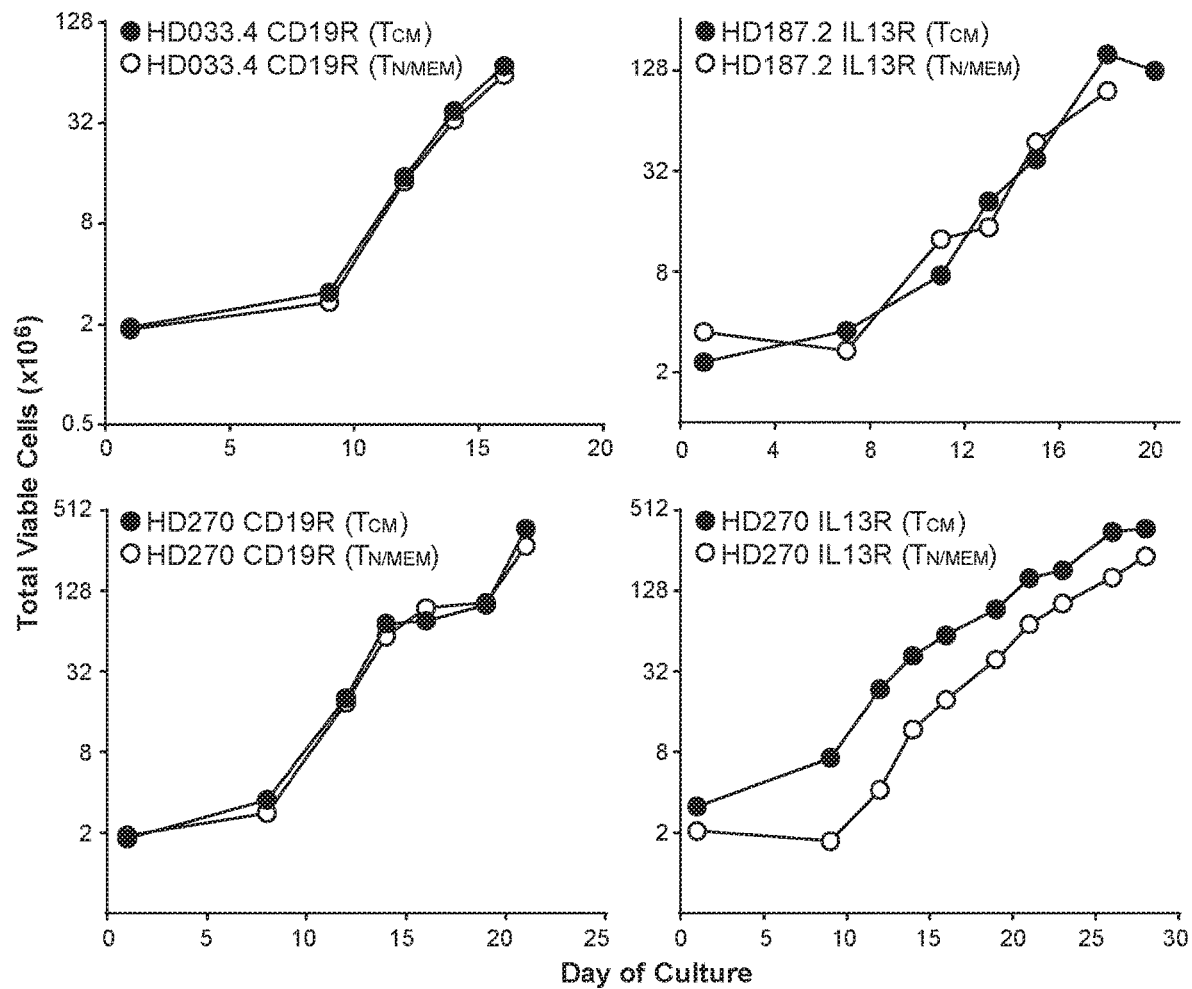
FIG. 5 depicts the results of a study of expansion of $T_{CM}$ and $T_{CM/SCM/N}$ cell populations. Viable cell numbers starting at the day of lentiviral transduction are depicted for cell products manufactured from 4 of the 5 donors, with $T_{CM}$-derived products represented by black circles, and $T_{CM/SCM/N}$-derived products represented by white squares. Log 2 scales were used for the Y-axes to better depict the doubling time of cells in culture.

Results of Viable Cell Number Analysis:

After bead stimulation and lentiviral transduction with CD19R(EQ)28Z-EGFRt_ePHIV7, the cell products were expanded under conditions that support T cell growth. Growth curves are depicted in FIGURE 5, and final cell numbers and fold expansion based on the total viable cells of each of the products are depicted in TABLE 3. Overall, fold expansion of $T_{CM/SCM/N}$-derived cell products was similar to that of their $T_{CM}$-derived counterparts.

TABLE 3

Expansion of Cell Products

| Product Name | Total viable cells (×10$^6$) Start | Total viable cells (×10$^6$) Final | Fold Expansion | Days in Culture |
|---|---|---|---|---|
| HD033.4 CD19R $T_{CM}$ | 1.9 | 70.8 | 37 | 16 |
| HD033.4 CD19R $T_{CM/SCM/N}$ | 1.9 | 62.1 | 33 | 16 |
| HD187.2 CD19R $T_{CM}$ | 4.8 | 26.8 | 6 | 10 |
| HD187.2 CD19R $T_{CM/SCM/N}$ | 9.0 | 48.2 | 5 | 10 |
| HD187.2 IL13R $T_{CM}$ | 2.3 | 128 | 56 | 20 |
| HD187.2 IL13R $T_{CM/SCM/N}$ | 3.5 | 96 | 27 | 18 |
| HD270 CD19R $T_{CM}$ | 1.8 | 373 | 207 | 21 |
| HD270 CD19R $T_{CM/SCM/N}$ | 1.9 | 278 | 146 | 21 |
| HD270 IL13R $T_{CM}$ | 3.1 | 373 | 120 | 28 |
| HD270 IL13R $T_{CM/SCM/N}$ | 2.0 | 232 | 116 | 28 |

Figure 6:
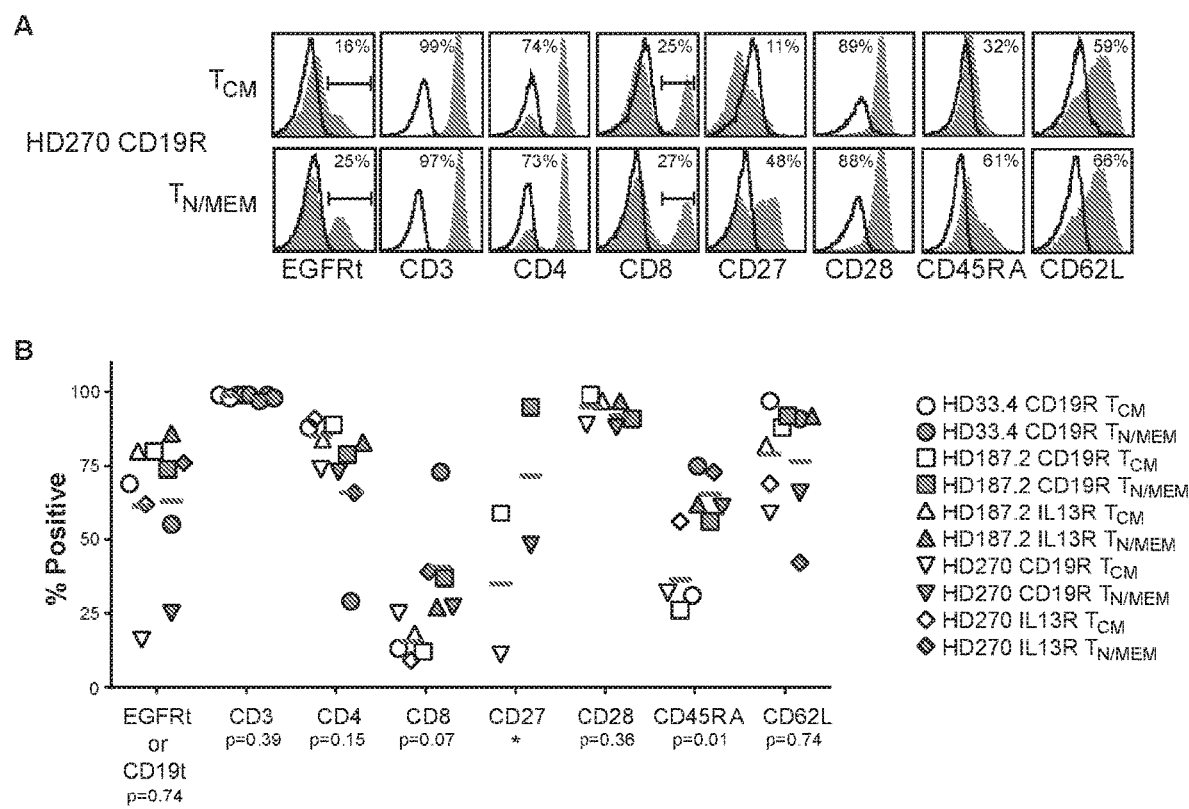
FIG. 6 depicts the results of an analysis of surface phenotype of $T_{CM}$ and $T_{CM/SCM/N}$ cell populations. $T_{CM}$ or $T_{CM/SCM/N}$-enriched cells were bead stimulated, transduced with CD19R(EQ)28Z-T2A-EGFRt_epHIV7 or IL13(EQ)BBZ-T2A-CD19t_epHIV7, and expanded ex vivo. Cells were then analyzed by flow cytometry after being stained with fluorochrome-conjugated reagents specific for the EGFRt or CD19t transduction markers, or for the T cell markers CD3, CD4 and CD8, the central memory T cell markers CD27, CD28 and CD62L, and the nave T cell marker CD45RA (grey histograms). Percentages of immunoreactive cells above control staining (open histograms) are indicated in each histogram of a representative $T_{CM}/T_{CM/SCM/N}$ pair (A) or are indicated as data points for each cell line in (B) with open symbols for the $T_{CM}$-derived products and grey symbols for the $T_{CM/SCM/N}$-derived products. Red bars depict the mean for each group, and p-values for paired Student's t-test comparisons of $T_{CM}$ vs. $T_{CM/SCM/N}$-derived cell products are indicated for each surface marker. *, P-value was not calculable for CD27 because too-few valued. Note that only shading, but not cell-line specific symbols, are depicted for CD3 staining in (B) due to overlap.

Final Product Flow Cytometric Analysis:

Flow cytometric analyses of each of the cell products following ex vivo expansion revealed that all of the final cyropreserved cell products would have passed our traditional product specifications of ≥80% CD3 for identity, and ≥10% EGFRt or CD19t for potency (FIG. 6A). Indeed, the $T_{CM/SCM/N}$-derived products from each donor were very similar to their corresponding $T_{CM}$-derived products in immunoreactivity for both CD3 and EGFRt/CD19t.

Flow cytometric analysis of other T cell markers (FIG. 6A) revealed that while all cell products have CD4 and CD8 T cell subsets, the $T_{CM/SCM/N}$-derived CAR T cell lines had a relatively higher proportion of CD8 cells compared to their $T_{CM}$-derived counterparts. Both $T_{CM}$-derived cell products and $T_{CM/SCM/N}$-derived cell products also expressed memory-associated markers CD27, CD28 and CD62L. However, CD27 expression was generally higher on the $T_{CM/SCM/N}$-derived products. Furthermore, CD45RA expression levels were also significantly higher on the $T_{CM/SCM/N}$-derived products.

Conclusion:

Together, these data obtained indicate that both $T_{CM}$- and $T_{CM/SCM/N}$-enriched populations can be CD3/CD28 bead stimulated, lentivirally transduced, and expanded in vitro. Since fold expansion was similar between the $T_{CM}$- and $T_{CM/SCM/N}$-derived counterparts, it is important to note that the ability to start with greater cell numbers of $T_{CM/SCM/N}$ may allow for a shorter expansion time to reach sufficient cell numbers for clinical use.

Flow cytometric analysis revealed that both $T_{CM}$ and $T_{CM/SCM/N}$ cell populations were transduced with similar efficiency to express the EGFRt or CD19t transgenes. Flow cytometric analysis also confirmed that both $T_{CM}$ and $T_{CM/SCM/N}$ cell populations express the T cell markers CD3, CD4, CD8, as well as T cell memory markers CD27, CD28 and CD62L. The higher percentages of CD45RA+ cells observed in $T_{CM/SCM/N}$ populations were as expected, since $T_{CM}$ cells were depleted of CD45RA in the selection process.

Example 5: In Vivo Efficacy of Intravenously Delivered $T_{CM}$ and $T_{CM/SCM/N}$ Cell Population Transduced with the CD19R(EQ)28Z-T2A-EGFRt_ePHIV7

A study was conducted to evaluate the in vivo efficacy of unselected PBMC, CD62L+ $T_{CM}$ cells and CD62L+ $T_{CM/SCM/N}$ cells transduced with lentiviral vector expressing a CAR targeted to CD19 (CD19R(EQ)28Z-T2A-EGFRt_ePHIV7 lentiviral vector) and expanded using methods suitable for clinical use. In vivo anti-tumor efficacy of these cells administered intravenously (i.v.) was examined in immunodeficient NSG mice using the CD19-expressing SUP-B15 human acute lymphocytic leukemia cell line, which has been engineered to express the green fluorescence protein (GFP) and firefly luciferase (ffLuc) reporter genes (PMID: 22407828).

Experimental Design:

$T_{CM}$-derived or $T_{CM/SCM/N}$-derived T cell lines that had been lenti-transduced with CD19R(EQ)28Z-T2A-EGFRt_ePHIV7 and expanded for 21 days were used in this study (see above, Examples 2 and 4). Freshly thawed CAR T cells administered i.v. were then evaluated for their ability to control the in vivo growth of i.v. engrafted Sup-B15 cells. Both tumor burden, as measured by Xenogen imaging, and T cell persistence, as measured by flow cytometric analysis of peripheral blood, were examined.

Overview of In Vivo Xenograft Studies:

Female NSG mice (10-12 weeks old) were irradiated with 300 rads at day 0. On day 1 mice were divided into groups (n=4) and left untreated, or treated i.v. (i.e., via the tail vein) with either 2.5×10$^6$ HD270-derived mock-transduced PBMC (no CAR), HD270 CD19R $T_{PBMC}$, HD270 CD19R $T_{CM}$, or HD270 CD19R $T_{CM/SCM/N}$. This translated to an average of 0.5×10$^6$ CAR+ cells of CD19R/EGFRt+ $T_{PBMC}$, CD19R/EGFRt+ $T_{CM}$ or 0.625×10$^6$ CD19R/EGFRt+ $T_{CM/SCM/N}$ being administered to each mouse as defined by the phenotypic analysis of the HD270 CD19R $T_{CM}$- and $T_{CM/SCM/N}$ derived lines. On day 2 mice were challenged i.v. with 2 tumor cells per 1 CAR+ T cell GFP:ffLuc+ Sup-B15 tumor cells. Growth of this human acute lymphobastic leukemia cell line was then monitored over time by Xenogen imaging and quantification of fire-fly luciferase (ffLuc) flux (photons/sec). At day 41, retro-orbital bleeding was performed, and the blood was evaluated for the presence of human CD3-expressing T cells by flow cytometric analysis, using a MACSQuant instrument and FCS Express software (De Novo Software, Los Angeles, CA).

Figure 7A:
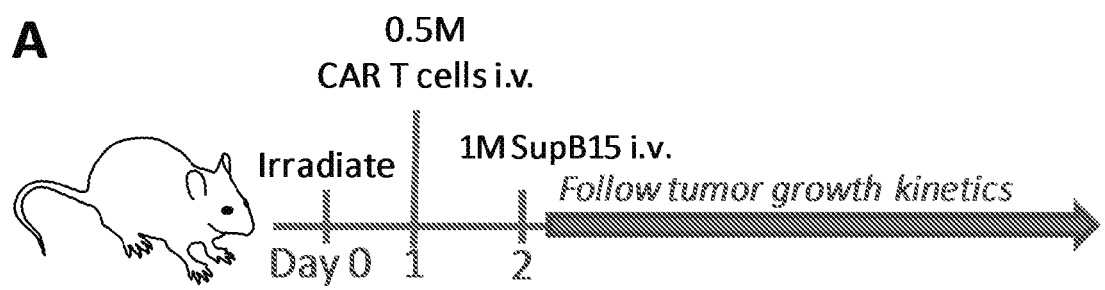
FIGS. 7A-C depict the results of a study assessing the therapeutic efficacy of CD19R $T_{CM}$ or CD19R $T_{CM/SCM/N}$ pre-treatment when challenged with Sup-B15 tumor cells. One day after irradiating the NSG mice, they were divided into groups (n=4) and left untreated, or treated i.v. with either 2.5×10⁶ mock-transduced PBMC (no CAR), CD19R $T_{CM}$ or CD19R $T_{CM/SCM/N}$ (approximately 0.5×10⁶ CAR+ cells). On day 2, mice were challenged i.v. with 0.7-1.0×10⁶ with ffLuc+ Sup-B15 tumor cells. M, million (FIG. 7A). Representative mice from each group showing relative tumor burden using Xenogen Living Image (FIG. 7B). Average Sup-B15 tumor growth in each group of mice over time as monitored by Xenogen imaging and quantification of ffLuc flux (photons/sec) (FIG. 7C).
Figure 7B:
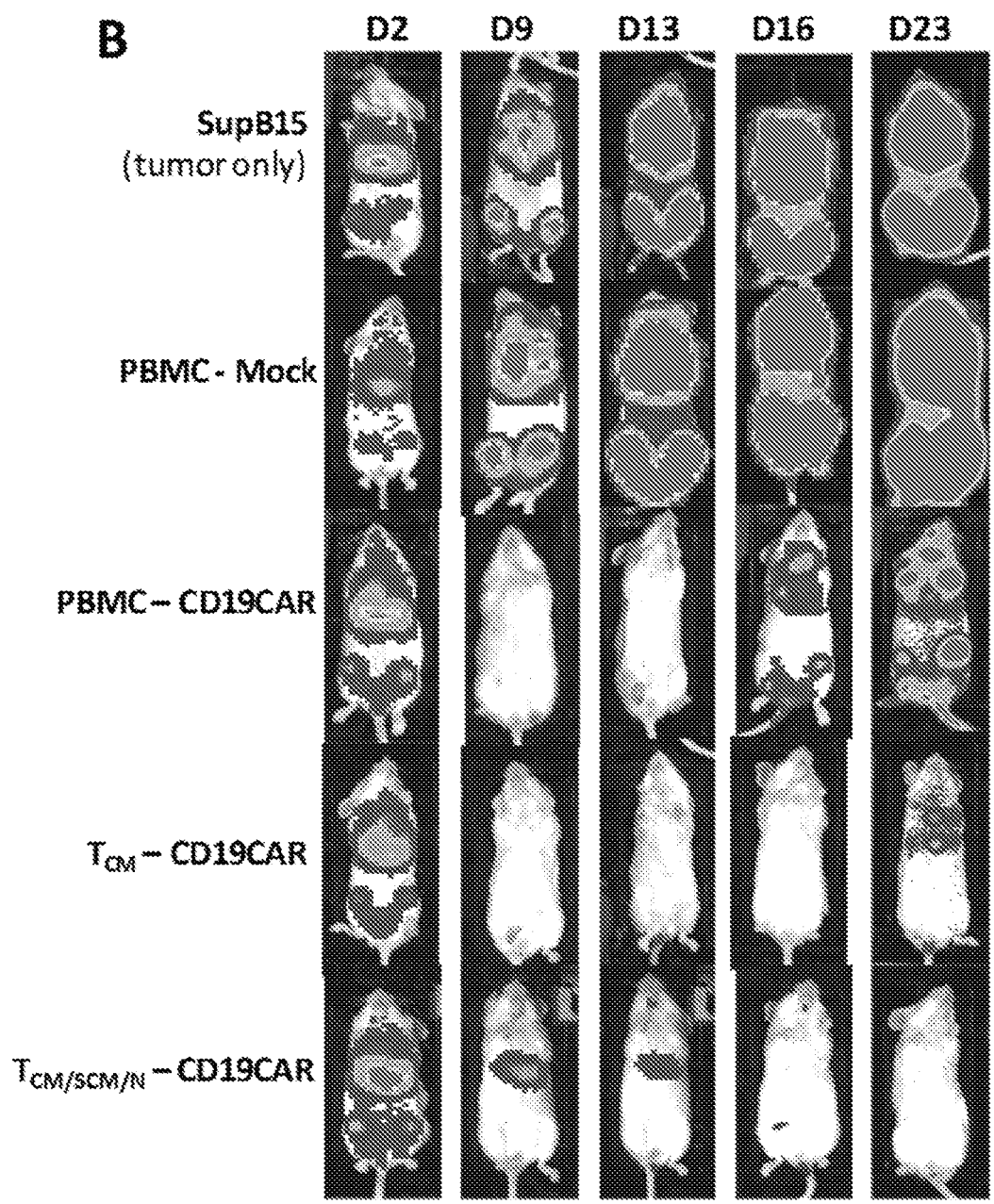
Figure 7C:
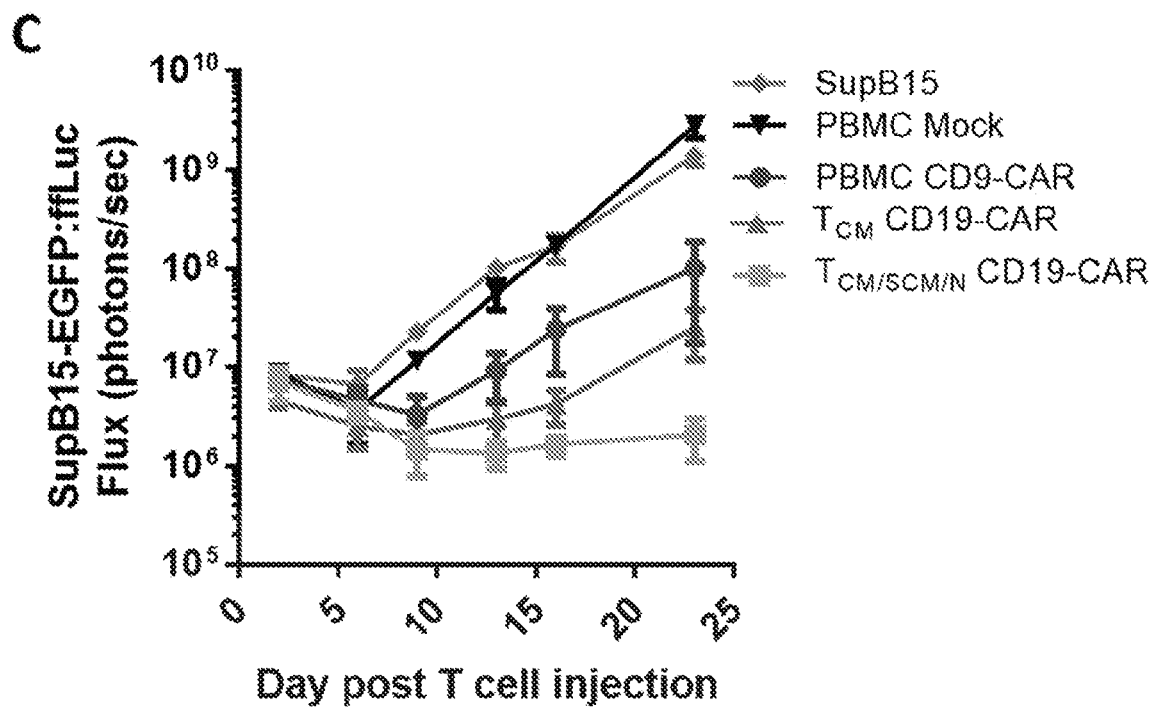

Evaluation of In Vivo Anti-Tumor Efficacy:

In FIG. 7A and FIG. 7B, which depict the results of this study, it can be seen that, i.v. administration of CD19R $T_{CM}$ cells showed only transient therapeutic benefit, while CD19R $T_{CM/SCM/N}$ cells exhibited more robust anti-tumor activity against the ffLuc+ Sup-B15 tumors.

Figure 8A:
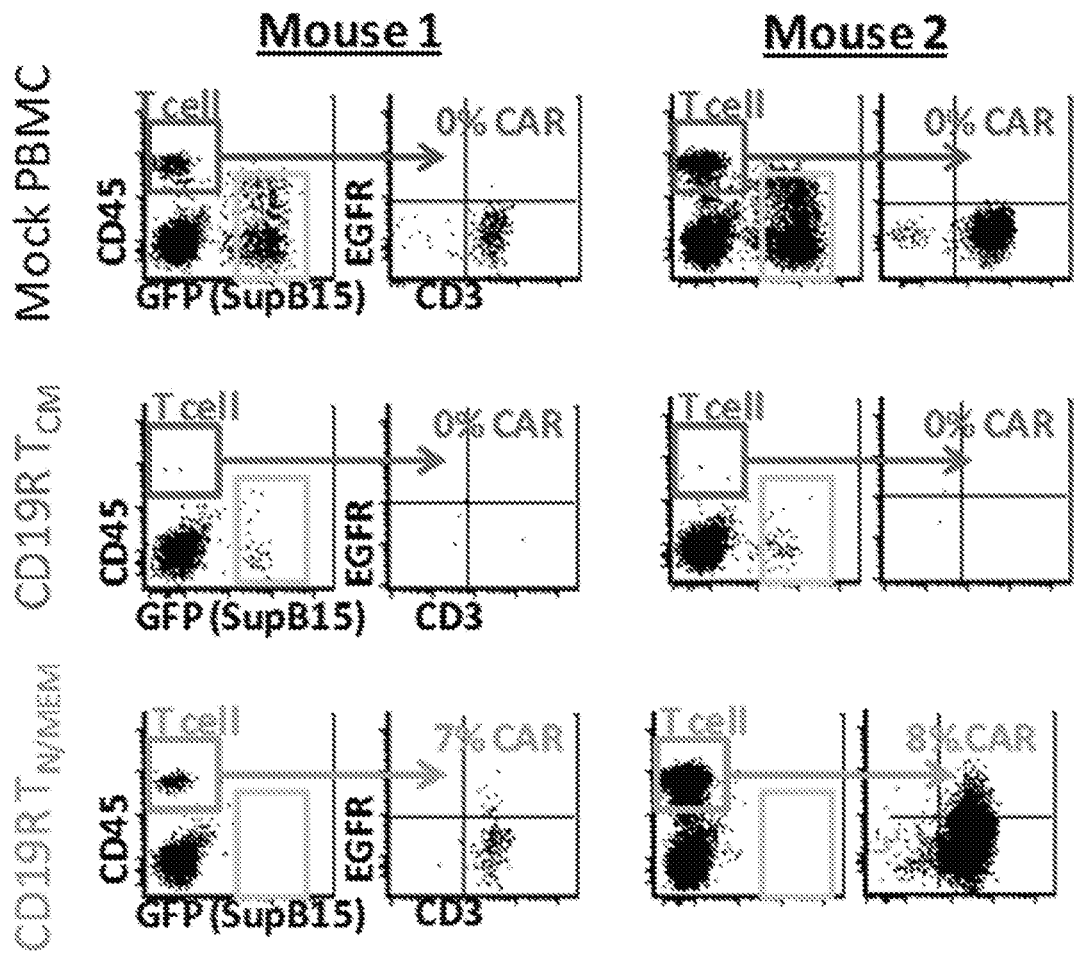
FIGS. 8A-B depict the results of study examining the presence of human T cells in the blood 41 days after i.v. pre-treatment with CD19R $T_{CM}$ or CD19R $T_{CM/SCM/N}$. One day after irradiating the NSG mice, they were divided into groups (n=4) and left untreated, or treated i.v. with either 2.5×10⁶ mock-transduced PBMC (no CAR), CD19R $T_{CM}$ or CD19R $T_{CM/SCM/N}$ (approximately 0.5×10⁶ CAR+ cells). On day 2, mice were challenged i.v. with 0.7-1.0×10⁶ with tumor GFP+ Sup-B15 tumor cells. At day 41, the blood of each mouse was evaluated for the presence of human CD45+CD3+ cells (i.e., human T cells) by flow cytometry. Representative flow cytometric analyses of each mouse are depicted (Mouse 1 and Mouse 2 are depicted in FIG. 8A; Mouse 3 and Mouse 4 are depicted in FIG. 8B), where huCD45-gated cells were further analyzed for expression of the CD3 T cell marker and the EGFRt transduction marker (% CAR+ based on upper right quadrant). Gold boxes are used to highlight the GFP+ SupB15 population.
Figure 8B:
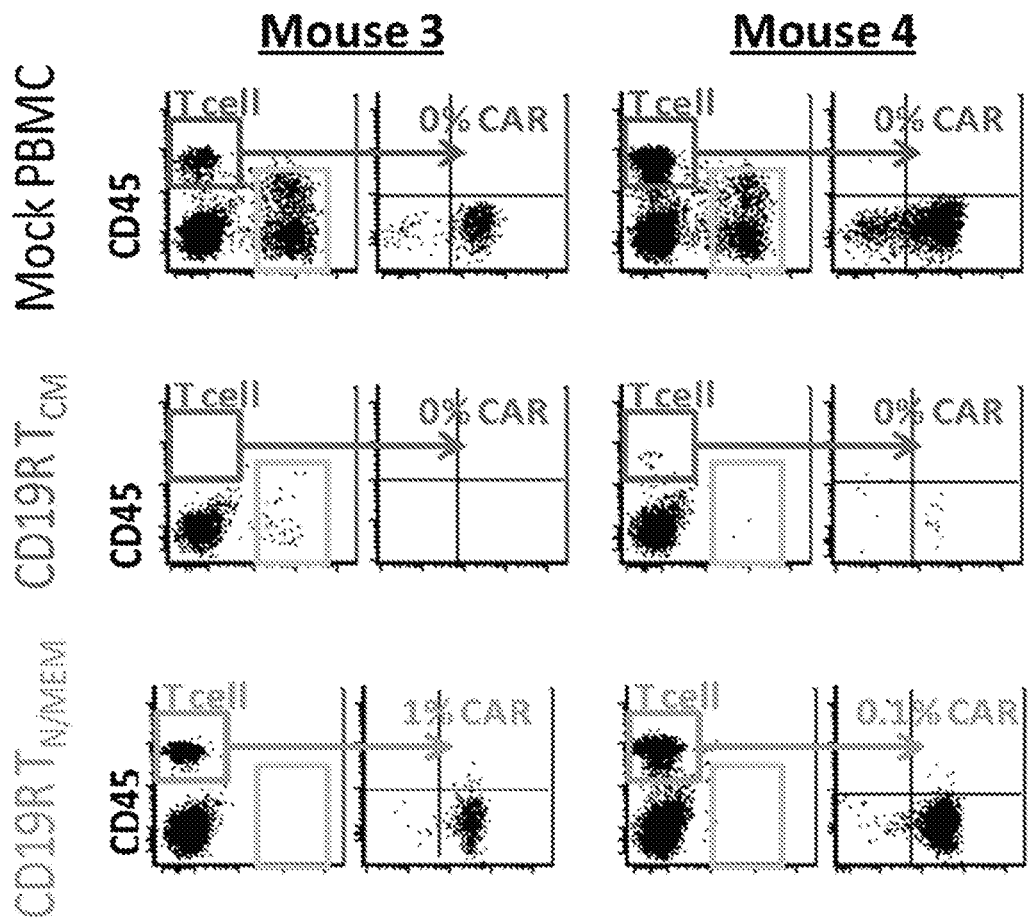

Analysis of T Cells in Peripheral Blood:

To evaluate the persistence of T cells in the peripheral blood in these mice, flow cytometric analysis was performed on retro-orbital bleeds collected 40 days after i.v. T cell administration. As depicted in FIG. 8, CAR+ T cells were only detectable at this timepoint in the mice that had received $T_{CM/SCM/N}$ cells. This presence of CAR+ human T cells correlated with the absence of GFP-expressing SupB15 tumor cells.

These studies demonstrate that in vivo anti-tumor efficacy can be observed with both CD19R $T_{CM}$- and CD19R $T_{CM/SCM/N}$-derived cell lines, with the anti-tumor responses of the CD19R $T_{CM/SCM/N}$ cell-treated mice being greater than that of the CD19R $T_{CM}$-treated mice. This efficacy correlated in part with the ability to detect CAR+ T cells in the blood of CD19R $T_{CM/SCM/N}$-treated mice.

Example 6: Effector Activity of $T_{CM}$ and $T_{CM/SCM/N}$ Cells Transduced with CD19R(EQ)28Z-T2A-EGFRt_epHIV7

A study was conducted to evaluate CD19-specific cytolytic activity, degranulation, and cytokine production of either CD62L+ central memory ($T_{CM}$) cells, or CD62L+ $T_{CM/SCM/N}$ cells that were transduced with the CD19R(EQ) 28Z-T2A-EGFRt_epHIV7 lentiviral vector and expanded using methods expected to be suitable for clinical use. Cytolytic activity was evaluated using a flow cytometry-based long term killing assay and a 5-hour degranulation assay. Cytokine production was evaluated by intracellular staining of the T cells after 5-hour co-culture with stimulator cells.

Experimental Design:

$T_{CM}$ cells and $T_{CM/SCM/N}$ cells were lenti-transduced with CD19R(EQ)28Z-T2A-EGFRt_epHIV7 and expanded for up to 21 days (See Examples 2 and 4). CD19-specific effector function of these cell products was evaluated by a long term killing assay which evaluates loss of target cells after 72 hours of co-incubation with effector T cells, and a 5-hour degranulation assay which evaluates cell surface CD107a mobilization as a marker of T cell cytotoxic activity. Evaluation of cytokine production by freshly thawed final cell products after 5 hours of in vitro stimulation was then conducted by flow cytometric analysis of intracellular staining for IFN-γ.

Brief Overview of Long Term Killing Assay:

Samples of each T cell product were thawed the day prior to the assay, rested overnight in the presence of 50 U/mL rhIL-2 and 0.5 ng/mL rhIL-15, and a 72-hour killing assay was then performed. Briefly, each T cell line and target cell line was counted and seeded at a 1:1 CAR+ T cell to target cell ratio into a 96-well tissue-culture treated, round-bottom plate specifically, 25,000:25,000 in 200 uL X-VIVO 15 media with 10% FBS per well. After 72 hours of culture, cells were collected with trypsinization, washed in cold FACS buffer, and then stained with anti-human CD45 to detect the T cells, with DAPI as a viability dye. Samples were run and analyzed on a MACSQuant (Miltenyi) instrument, and numbers of viable immunoreactive cells were calculated via FlowJo software (FlowJo, LLC, Ashland, OR). Final results were then graphed as percentages of CD45-negative, forward scatter high tumor cells remaining in the cultures when compared to that of mock-transduced effector cell co-cultures which had been normalized to 100%.

Brief Overview of Degranulation Assay and Intracellular Cytokine Analysis:

Samples of each T cell product were freshly thawed, and a 5-hour degranulation assay was then performed. T cells were counted and resuspended in media containing Golgi Stop, a protein transport inhibitor that blocks the reabsorption of CD107a from the cell surface. The T cells were then seeded at a 1:1 ratio with tumor cells (with Golgi Stop) in a 96-well plate. To each well, an antibody against CD107a was added, and then the plate was incubated for 5 hours at 37° C. Additional antibodies then were added to each condition to stain for CD45, CD4, CD8, and the EGFRt transgene. Cells were then fixed and permeabilized for staining with antibody specific for IFN-γ or isotype control antibody. Samples were run and analyzed on a MACSQuant (Miltenyi) instrument, and percentages of immunoreactive cells were calculated via FlowJo software (FlowJo, LLC, Ashland, OR).

Figure 9:
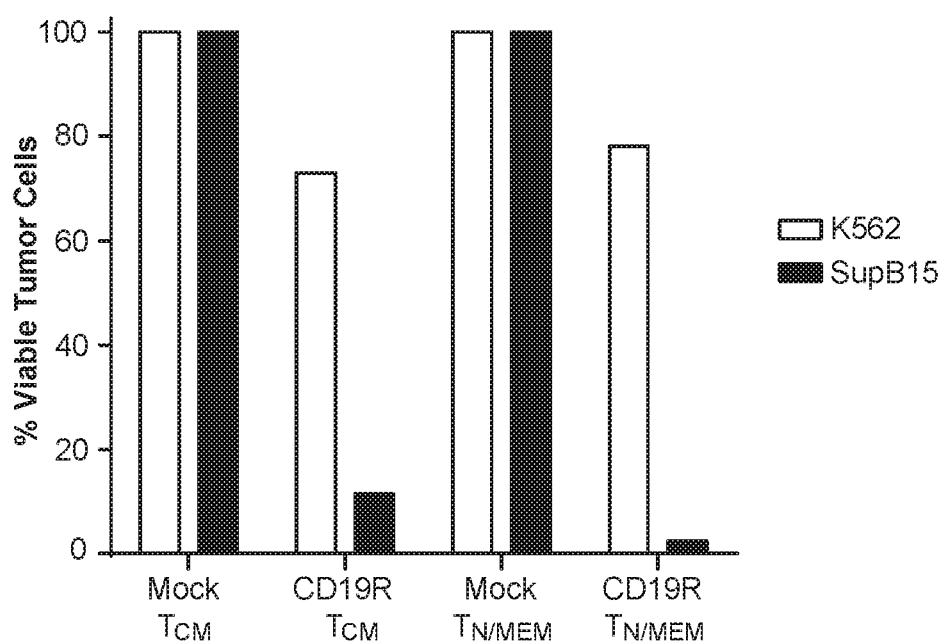
FIG. 9 depicts the results of long term killing assays performed with $T_{CM}$-cells or $T_{CM/SCM/N}$ cells that had been mock-transduced or transduced with CD19R(EQ)28ZEGFRt_epHIV7 as effectors and either CD19-negative K562 cells (white bars) or CD19+ SupB15 cells (black bars) as targets. Percentages of viable target cells (CD45-negative, FSC high) remaining after 72 hours compared to mock effector co-cultures that were normalized to 100% are depicted.

Determination of Cytolytic Activity by Long Term Killing Assay:

$T_{CM}$ cells and $T_{CM/SCM/N}$ cells that had either been mok-transduced or transduced with CD19R(EQ)28Z-T2A-EGFRt_epHIV7 were each plated with either CD19-negative K562 cells or CD19+ SupB15 cells for 72 hours. Results are presented in FIG. 9 and show similar loss of detectable SupB15 targets in the cultures with both CD19R $T_{CM}$ and CD19R $T_{CM/SCM/N}$ cells when compared to their respective mock-transduced controls. Indeed, this loss of SupB15 targets was significantly greater than that observed with K562 targets, further supporting the CD19-specificity of this cytolytic activity.

Figure 10:
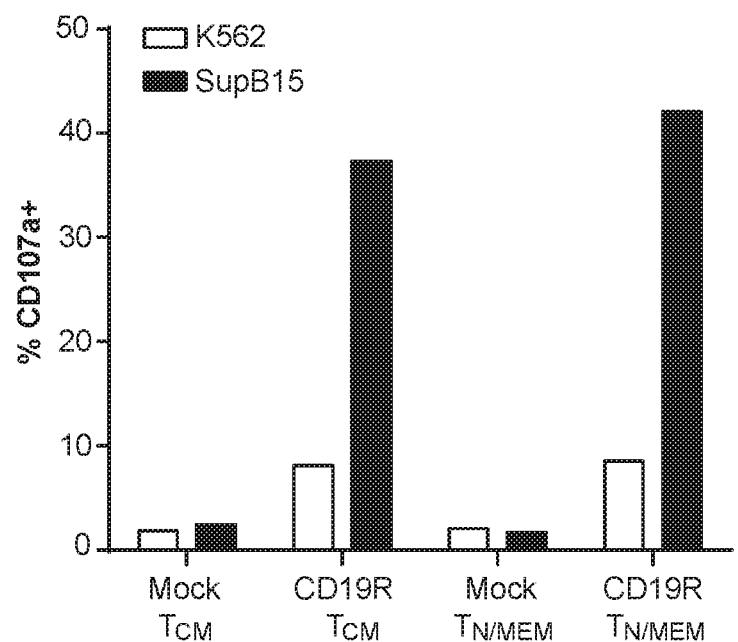
FIG. 10 depicts the results of five hour degranulation assays performed with $T_{CM}$-cells or $T_{CM/SCM/N}$ cells that had been mock-transduced or transduced with CD19R(EQ)28ZEGFRt_epHIV7 as effectors and either CD19-negative K562 cells (white bars) or CD19+ SupB15 cells (black bars) as stimulators. Percentages of CD45/CD8/EGFRt-gated cells that were immunoreactive for CD107a are indicated.

Determination of Effector Activity by Degranulation Assay:

$T_{CM}$ cells and $T_{CM/SCM/N}$ cells that had either been mock-transduced or transduced with CD19R(EQ)28Z-T2A-EGFRt_epHIV7 were each plated with either CD19-negative K562 cells or CD19+ SupB15 cells. Results are presented below (FIG. 10) and demonstrate that the CD8+ CD19R $T_{CM}$ and CD8+ CD19R $T_{CM/SCM/N}$ cells exhibit similar CD19-specific degranulation (i.e., CD107a expression) upon stimulation with SupB15 cells. The antigen-specificity of this activity is further evidenced by examining the mock-transduced cells (FIG. 10) which are not stimulated to degranulate by the CD19-expressing SupB15 cells.

Figure 11:
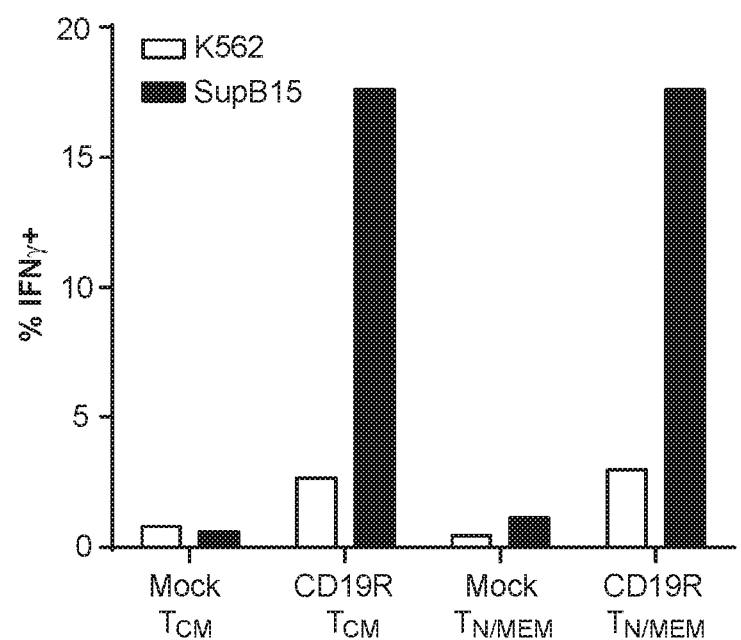
FIG. 11 depicts the results analysis of IFNγ production by $T_{CM}$ cells or $T_{CM/SCM/N}$ cells that had been mock-transduced or transduced with CD19R(EQ)28ZEGFRt_epHIV7 Five hour co-cultures were performed with $T_{CM}$-derived or $T_{CM/SCM/N}$-derived cell products that had been mock-transduced or transduced with CD19R(EQ)28ZEGFRt_epHIV7 as effectors and either CD19-negative K562 cells (white bars) or CD19+ SupB15 cells (black bars) as stimulators. Percentages of CD45/CD8/EGFRt-gated cells that were immunoreactive for IFN-γ are indicated.

Determination of Effector Activity by Intracellular Cytokine Assay:

$T_{CM}$ cells and $T_{CM/SCM/N}$ cells that had either been mock-transduced or transduced with CD19R(EQ)28Z-T2A-EGFRt_epHIV7 were each plated with either CD19-negative K562 cells or CD19+ SupB15 cells. Results are presented in FIG. 11 and demonstrate that the CD8+ CD19R $T_{CM}$ and CD8+ CD19R $T_{CM/SCM/N}$ exhibit similar CD19-specific, intracellular IFN-γ profiles. The antigen-specificity of this activity is further evidenced by examining the mock-transduced cells 0 which are not stimulated to express IFN-γ by the CD19-expressing SupB15 cells.

These data confirmed that both $T_{CM}$ cells and $T_{CM/SCM/N}$ cells that had been transduced with CD19R(EQ)C28Z-T2A-EGFRt_epHIV7 exhibit cytolytic activity, degranulation and cytokine (i.e., IFN-γ) production upon co-culture with CD19-expressing target cells.

Example 7: Effector Activity of $T_{CM}$ and $T_{CM/SCM/N}$ Cells Transduced with IL13(EQ)BBZ-T2A-CD19t_epHIV7

A study was conducted to evaluate the in vivo efficacy of CD62L+ $T_{CM}$ cells and CD62L+ $T_{CM/SCM/N}$ cells transduced with lentiviral vector expressing a CAR targeted to IL13Rα2. The CAR includes a human IL-13 variant and is expressed by a lentiviral vector (IL13(EQ)BBZ-T2A-CD19t_epHIV7). The cell populations expressing this vector were prepared as described above in Example 4 and assessed in a murine model of glioblastoma in immunodeficient NSG mice using the IL13Rα2+ primary low-passage GBM tumor sphere line PBT030-2, which has been engineered to express the firefly luciferase (ffLuc) reporter gene.

Briefly, male NSG mice (10-12 weeks old) were stereotactically injected with $1 \times 10^5$ ffLuc+ PBT030-2 cells in both the right and left contralateral hemispheres on day 0 and allowed to engraft for 6 days. Groups of mice were then left untreated or treated with $1 \times 10^6$ CAR+ IL13(EQ)BBζ/CD19t+ $T_{CM/SCM/N}$, CAR+ IL13(EQ)BBζ/CD19t+ $T_{CM}$, mock transduced $T_{CM/SCM/N}$ or mock transduced $T_{CM}$. PBT030-2 tumor growth was monitored over time by Xenogen imaging and quantification of ffLuc flux (photons/sec).

Figure 12:
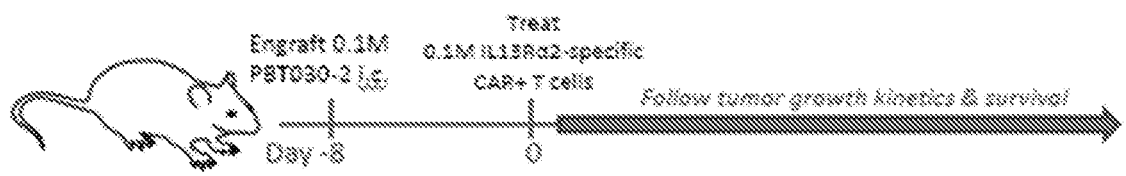
FIG. 12 depicts the results of a study of efficacy of IL13 CAR expressed by various T cell populations.
Figure 12:
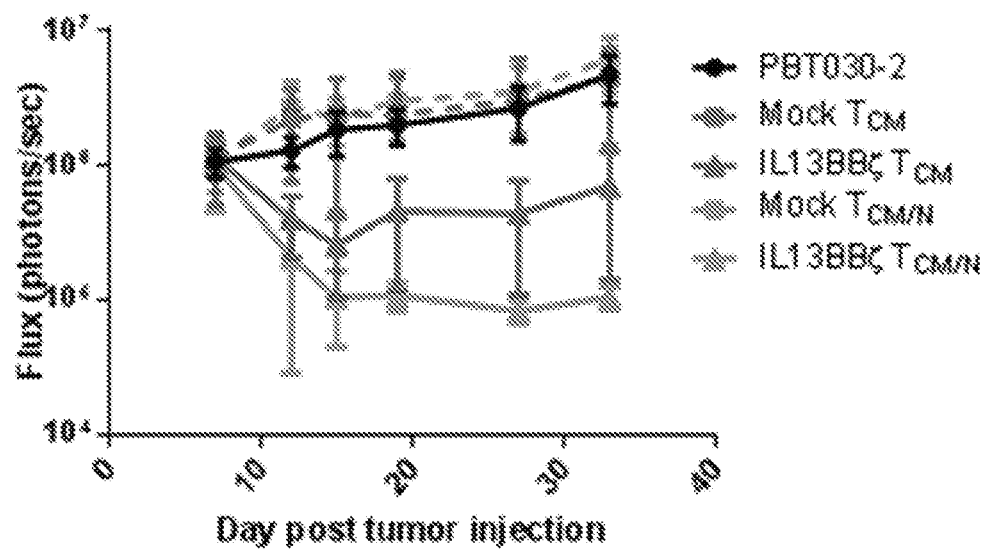
Figure 12:
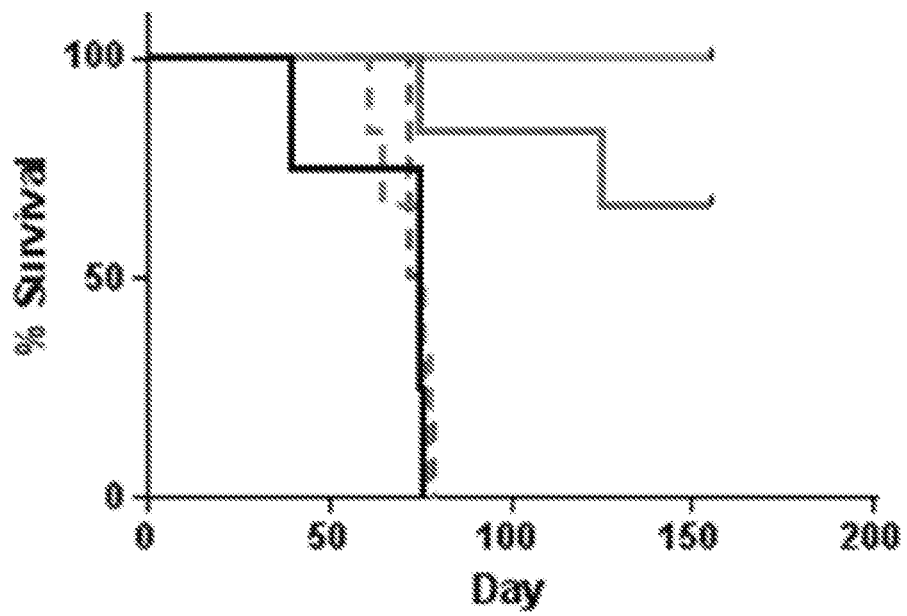

As shown in FIG. 12, $T_{CM/SCM/N}$ transfected with a CAR directed against IL-IL13Rα2 were superior to similarly transfected $T_{CM}$ with respect to suppression of tumor growth and with respect to survival in a murine intratumoral glioblastoma model.

What is claimed is:

1. A method for preparing a population of human cells comprising T cells, wherein the T cells comprise central memory T cells, memory stem T cells, and naïve T cells, wherein greater than 40% of the cells are CD45RA+ and greater than 70% are CD62L+, comprising;
   (a) providing sample of human PBMC;
   (b) treating the sample of human PBMC to deplete cells expressing CD25 and cells expressing CD14 to prepare a depleted cell population; and
   (c) treating the depleted cell population to enrich for cells expressing CD62L, thereby preparing a population of human cells comprising T cells, wherein the T cells comprise central memory T cells; memory stem T cells, and naïve T cells, wherein greater than 40% of the cells are CD45RA+ and greater than 70% are CD62L+,
   wherein the method does not comprise a step of depleting cells expressing CD45RA.

2. The method of claim 1 further comprising activating the population of human cells comprising T cells, wherein the T cells comprise central memory T cells; memory stem T cells, and naïve T cells, wherein greater than 40% of the cells are CD45RA+ and greater than 70% are CD62L+ and transducing or transfecting the activated cells with a recombinant nucleic acid molecule to provide a population of T cells comprising T cells harboring a recombinant nucleic acid molecule.

3. The method of claim 2 further comprising culturing the population of human cells comprising T cells harboring a recombinant nucleic acid molecule.

4. The method of claim 3, wherein the culturing step comprises culturing in the presence of exogenous IL-2 and exogenous IL-15.

5. The method of claim 2, wherein the activating step comprises exposing the cells to an anti-CD3 antibody and an anti-CD28 antibody.

6. The method of claim 2, wherein the recombinant nucleic acid molecule is a viral vector.

7. The method of claim 6, wherein the viral vector comprises a nucleotide sequence encoding a chimeric antigen receptor or a T cell receptor.

* * * * *